United States Patent [19]
Talamonti

[11] Patent Number: 5,890,516
[45] Date of Patent: Apr. 6, 1999

[54] STOMACH SUCTION PUMP CONNECTOR VALVE

[76] Inventor: Anthony R. Talamonti, 1710—41st Ave., Kenosha, Wis. 53144

[21] Appl. No.: 689,647

[22] Filed: Aug. 12, 1996

[51] Int. Cl.⁶ .................................................... F17D 65/20
[52] U.S. Cl. ......................... 137/605; 604/118; 604/119; 604/35
[58] Field of Search ............................. 137/605; 604/118, 604/119, 121, 35, 30

[56] References Cited

U.S. PATENT DOCUMENTS

| | | | |
|---|---|---|---|
| 3,071,402 | 1/1963 | Lasto et al. | 137/625.25 |
| 3,469,582 | 9/1969 | Jackson | 604/119 |
| 3,645,497 | 2/1972 | Nyboer | 251/148 |
| 3,834,388 | 9/1974 | Sauer | 604/119 |
| 3,885,565 | 5/1975 | Satchell | 604/119 |
| 4,504,266 | 3/1985 | Harle | 604/118 |
| 4,758,224 | 7/1988 | Siposs | 604/118 |
| 4,790,832 | 12/1988 | Lopez | 604/283 |
| 4,919,129 | 4/1990 | Weber, Jr. et al. | 604/35 |

*Primary Examiner*—Denise L. Ferensic
*Assistant Examiner*—Joanne Y. Kim
*Attorney, Agent, or Firm*—Jansson, Shupe, Bridge & Munger, Ltd.

[57] ABSTRACT

A disposable device for controlling the rate of suction to and from a bodily organ, such as the stomach, during a lavage procedure that involves the use of a movable controller that slides back and forth over an opening in the main body of the device. The interior opening of the device which is placed in a flowline that extends from the stomach upstream to a downstream collection vessel has a tapered flow path that allows for the uninterrupted flow of pill fragments or stomach contents through the flowline. A lateral flow path that extends from an opening in the exterior of the main body to the main flow path enables an operator to vary the suction pressure to or from the patient by varying the size of the exterior opening through the use of the movable controller.

12 Claims, 5 Drawing Sheets

1

STOMACH SUCTION PUMP CONNECTOR VALVE

FIELD OF THE INVENTION

This invention relates generally to suction valves and more particularly, to a device for controlling the rate of suction to and from the stomach during gastric lavage.

BACKGROUND OF THE INVENTION

Acute poisoning remains a common cause of morbidity and even mortality in children and adults. However, if ingested poison can be removed from the gastrointestinal tract before being absorbed, the risk of severe poisoning is prevented or reduced. Stomach emptying is among the most time-honored and widely accepted medical treatments for ingested poisons. Because of this, physicians have routinely treated poison and overdose patients by performing gastric lavage.

A major problem associated with gastric lavage involves the clogging of the evacuation devices used to perform the procedure. Additionally, in-wall vacuum systems used in the procedure generally provide more steady suction than is necessary. Because of this, a valve is required to regulate the flow from the patient to the vacuum source.

The problem resulting from the use of a suction control valve is that the valve and hose connectors tend to clog and plug-up with stomach contents or pill fragments. Because of this, many hospitals have abandoned the in-wall vacuum units in favor of a hand plunger device. Use of the hand plunger, however, creates its own unique problems in that the plunger unit is costly, difficult to operate, and requires the use of an additional technician.

U.S. Pat. No. 4,790,832 (Lopez) describes a system for administering medication nasally to a patient and involves the use of a plastic connector having a series of flanges of increasing diameter that allows it to be inserted into flexible plastic gastric tubes of different sizes. The plastic connector used with this system—which can also be connected to suction when it is desired to remove fluid from a patient's stomach—highlights some of the problems identified above in that the tapering of the connection ends results in a void between the inside wall of the gastric tube and the outside wall of the connector. This void often fills with pill fragments or stomach contents that clog the evacuation tube.

A device that would reduce the number of qualified personnel required to perform a gastric lavage, allow an operator to vary the degree of suction to or from a patient, reduce the possibility of line obstruction, provide for easy clearing of pill fragments or stomach contents, be less costly, and disposable would be an important advancement in the art.

OBJECTS OF THE INVENTION

It is an object of the invention to provide a stomach suction control device that overcomes some of the problems and shortcomings of the prior art.

Another object of the invention is to provide a stomach suction control device that capable of varying the amount of suction to or from the patient.

Another object of the invention is to provide a stomach suction control device that reduces the number of qualified personnel required to perform a gastric lavage.

Yet another object of the invention is to provide a stomach suction control device that is disposal.

Still another object of the invention is to provide a stomach suction control device that reduces or eliminates the possibility of clogging the evacuation tube. How these and other objects are accomplished will become apparent from the following descriptions and from the drawings.

SUMMARY OF THE INVENTION

The invention is a stomach suction control device that is placed in a flowline that extends from a stomach upstream to a vacuum source downstream and is comprised of a main body having upstream and downstream end portions engageable with the flowline in fluid-flow relation thereto and having a middle exterior surface therebetween. The main body of the device defines and extends along a main flow path while a lateral flow path extends from the main flow path to an opening in the middle exterior surface of the main body. The device also includes a controller attached to the main body and movable with respect to the opening to control whether, and the extent to which, the opening is blocked thereby.

In a preferred embodiment of the invention, the controller is fitted around the middle exterior surface of the device in such a way as to allow the controller to move thereon over the opening. In a highly preferred embodiment, the controller is fitted around the middle exterior surface in a manner that allows the controller to move back and forth on the main body along the direction of the main flow path.

In a preferred embodiment of the invention, the relative dimensions of the opening in the middle exterior surface and the controller are such that the controller can completely occlude the opening or the opening can be completely unoccluded by the controller. In such embodiment, the middle exterior surface of the device is cylindrical and the controller encircles the middle exterior surface.

In a highly preferred embodiment, the middle exterior surface is cylindrical and the controller partially encircles the middle exterior surface.

The controller of the device involved in the invention is frictionally engaged with the middle exterior surface of the main body such that it remains stationary with respect to the main body except when manually moved. In a preferred embodiment of the invention, the controller is fitted around the middle exterior surface of the main body in a manner that allows the controller to move back and forth on the main body along the direction of the main flow path. In this embodiment, the middle exterior surface is cylindrical and the controller encircles the middle exterior surface. In a highly preferred embodiment, the controller partially encircles the middle exterior surface.

The main body of the device includes first and second stops which are affixed at the ends of the middle exterior surface and define the range of movement of the controller along the middle exterior surface. These stops are spaced far enough apart such that given the relative dimensions of the opening in the middle exterior surface and the controller, the controller can completely occlude the opening or the opening can be completely unoccluded by the controller.

The upstream end portion of the main body is tapered and has an inner wall and an outer wall that converge so as to form a "sharp" edge that fits snug against an inside wall of a pliable tube extending along the flowline to the stomach. Once fitted together, the upstream end portion of the main body is closely adjacent to the inside wall of the pliable tube thereby reducing the possibility of particles becoming clogged along the flowline.

In a preferred embodiment of the invention, the main flow path is continuously tapered from the upstream end portion of the main body to the downstream end of the main body so that the main flow path is substantially free of impediments whereby particles cannot collect along the main flow path. In this embodiment, the lateral flow path is angled so as to allow for the easy insertion of a cleaning device.

In yet another embodiment of the invention, a bodily organ other than the stomach can be used to define the upstream limit of the main flow path.

DETAILED DESCRIPTIONS OF THE PREFERRED EMBODIMENTS

Figure 1:
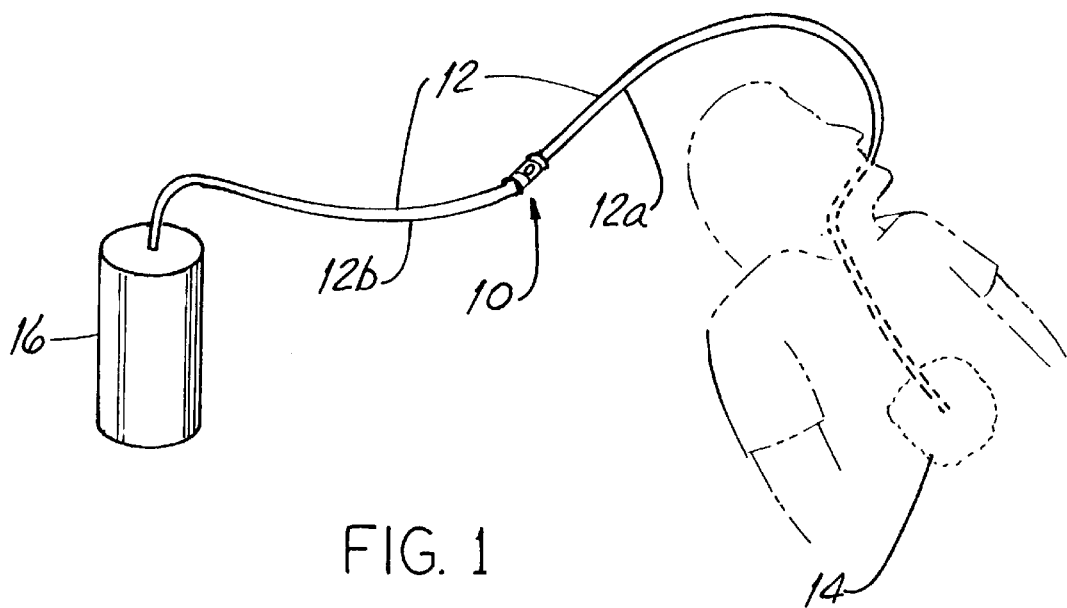
FIG. 1 is a schematic drawing showing the position of the suction pump control valve in a flowline between the stomach and a collection reservoir.
Figure 2:
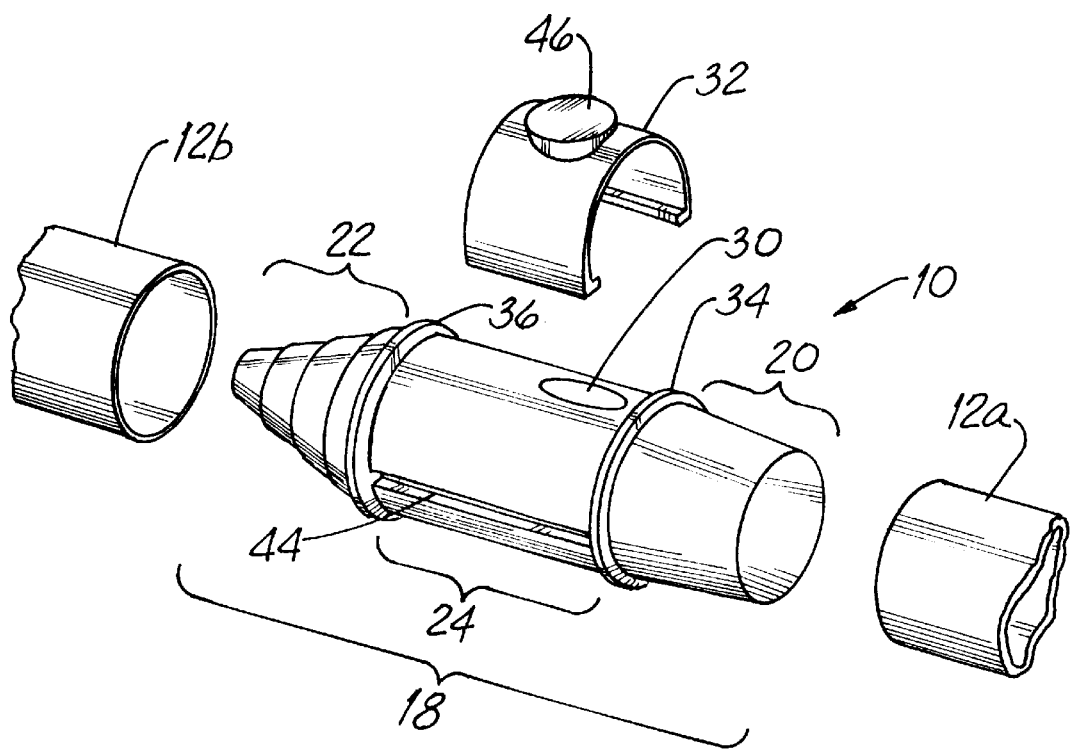
FIG. 2 is a perspective of the suction pump connector valve and its relationship to the flowline.
Figure 5:
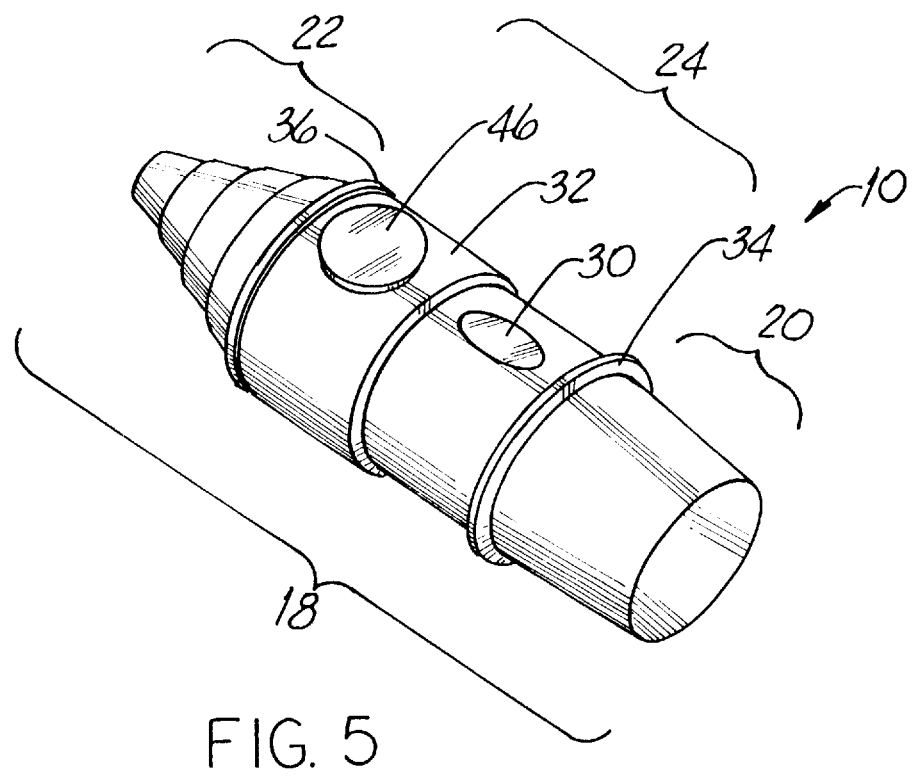
FIG. 5 is perspective of the suction pump connector valve showing the controller in the fully open position.
Figure 6A:
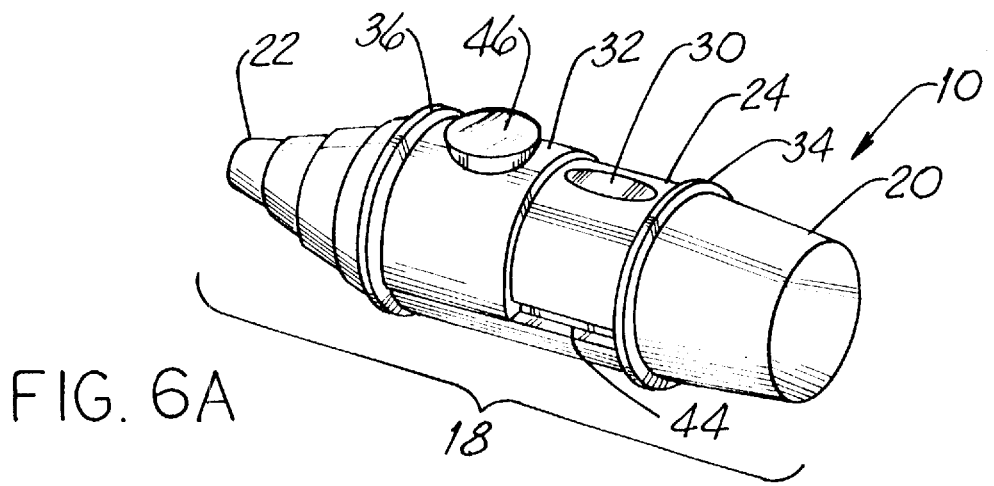
FIG. 6(a) is a perspective of the suction pump connector valve showing the controller positioned so that the opening in the main body is unoccluded.
Figure 6B:
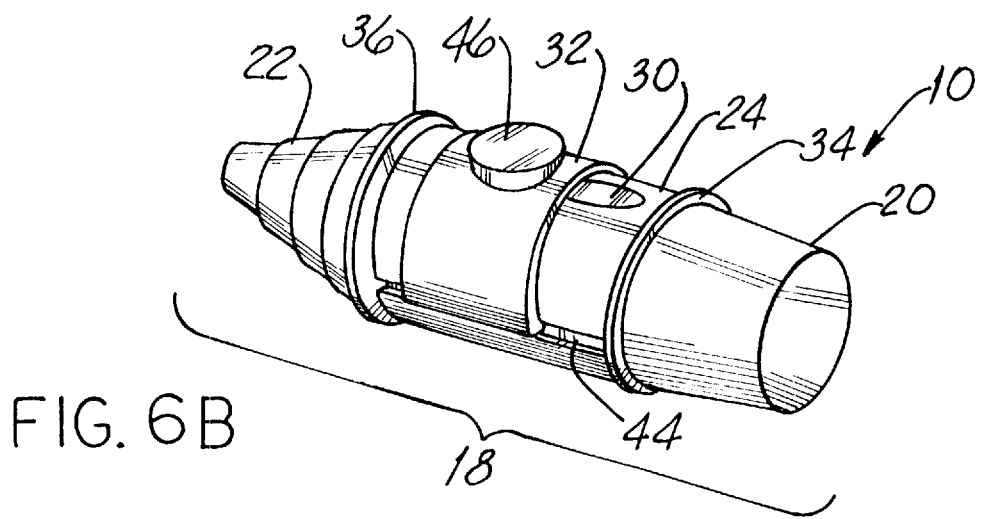
FIG. 6(b) is a perspective of the suction pump connector valve showing the controller partially occluding the opening in the main body.
Figure 6C:
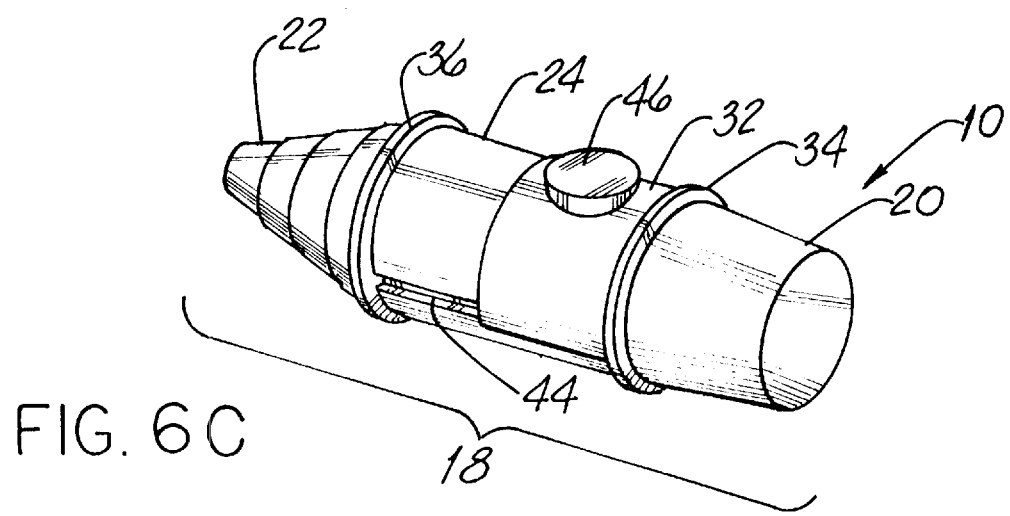
FIG. 6(c) is a perspective of the suction pump connector valve showing the controller fully occluding the opening in the main body.

FIGS. 2, 5, and 6(a–c), show a device 10 for controlling suction from the stomach or some other bodily organ during a lavage procedure. The stomach suction control device 10 that is the subject of this invention is placed in a flowline 12 that extends from a stomach 14 upstream to a vacuum source 16 downstream as shown in FIG. 1. The flowline 12 is defined by an upstream portion of pliable tubing 12a, the main flow path 26 through the suction control device 10, and a downstream portion of pliable tubing 12b. In certain embodiments, not particularly preferred, the suction control device can effectively be made part of the gastric tube and integrated therewith.

Figure 3:
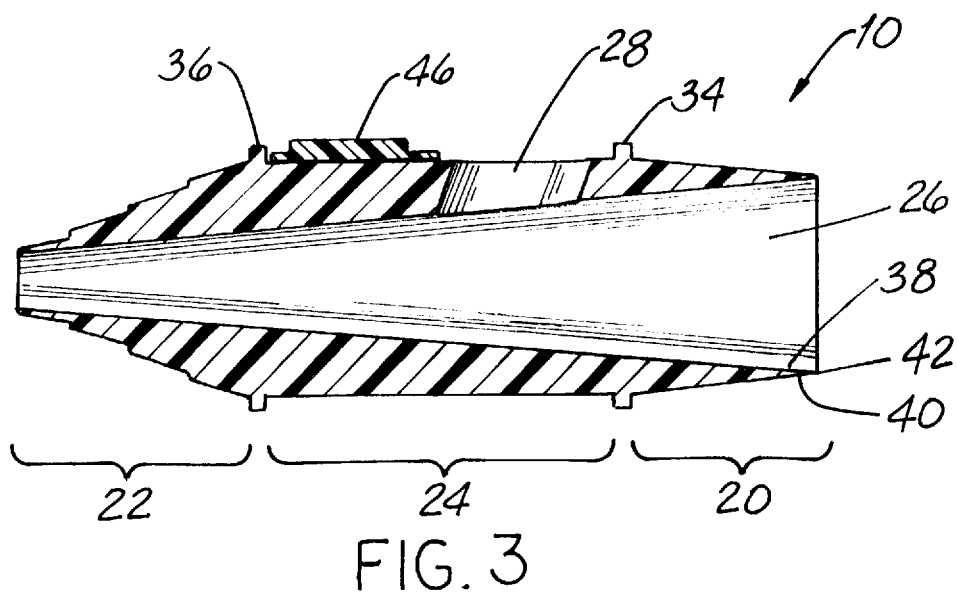
FIG. 3 is a sectional view of the suction pump connector valve showing the lateral flow path and the tapered channel of the main flow path.

As shown in FIG. 2, the preferred suction control device 10 is comprised of an injection/blow molded plastic main body 18 having upstream and downstream end portions 20, 22 engageable with the flowline 12 in fluid-flow relation thereto and having a middle exterior surface 24 therebetween. As shown in FIG. 3, the main body 18 of the device defines and extends along a main flow path 26 while a lateral flow path 28 extends from the main flow path 26 to an opening 30 in the middle exterior surface 24 of the main body 18. The device 10 also includes a controller 32, as shown in FIGS. 2 and 5, attached to the main body 18 and movable with respect to the opening 30 to control whether, and the extent to which, the opening 30 is blocked thereby.

In a preferred embodiment of the invention, the controller 32 is fitted around the middle exterior surface 24 of the device 10 in such a way as to allow the controller 32 to move thereon over the opening 30 thereby controlling the rate of suction to the patient. FIG. 5 shows a highly preferred embodiment, where the controller 32 is fitted around the middle exterior surface 24 in a manner that allows the controller 32 to move back and forth on the main body 18 along the direction of the main flow path 26.

FIGS. 6(a–c) show a preferred embodiment of the invention, where the relative dimensions of the opening 30 in the middle exterior surface 24 and the controller 32 are such that the controller 32 can completely occlude the opening 30 or the opening 30 can be completely unoccluded by the controller 32. In such embodiment, the middle exterior surface 24 of the device 10 is cylindrical and the controller 32 encircles the middle exterior surface 24.

Figure 4:
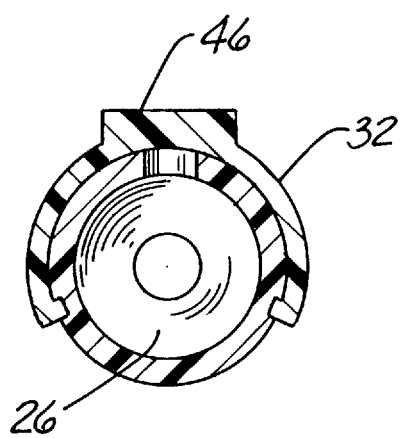
FIG. 4 is a sectional view of the suction pump connector valve looking down the main flow path.

In a highly preferred embodiment, the middle exterior surface 24 is cylindrical and the controller 32 partially encircles the middle exterior surface 24 as shown in FIGS. 2 and 4. In yet another highly preferred embodiment, as shown in FIGS. 2 and 6(a–c), the controller 32 moves back and forth on the main body 18 in a track 44 that is cut into the sides of the main body 18.

The controller 32 of the device 10 involved in the invention is frictionally engaged with the middle exterior surface 24 of the main body 18 such that it remains stationary with respect to the main body 18 except when manually moved. In a highly preferred embodiment, a thumb grip 46 is attached to the controller 32 to aid in its movement. As used herein, frictionally engaged is defined as being unable to move when acted on by gravity alone.

In a preferred embodiment of the invention, the controller 32 is fitted around the middle exterior surface 24 of the main body 18 in a manner that allows the controller 32 to move back and forth on the main body 18 along the direction of the main flow path 26 as shown in FIGS. 6(a–c). In this embodiment, as shown in FIG. 5, the middle exterior surface 24 is cylindrical and the controller 32 encircles the middle exterior surface 24. In a highly preferred embodiment, as shown in FIG. 2, the controller 32 partially encircles the middle exterior surface 24.

The main body 18 of the device 10 includes first and second stops 34, 36 which are affixed at the ends of the middle exterior surface 24 and define the range of movement of the controller 32 along the middle exterior surface 24. As shown in FIGS. 6(a–c), these stops 34, 36 are spaced far enough apart such that given the relative dimensions of the opening 30 in the middle exterior surface 24 and the controller 32, the controller 32 can completely occlude the opening 30 or the opening 30 can be completely unoccluded by the controller 32.

Figure 7:
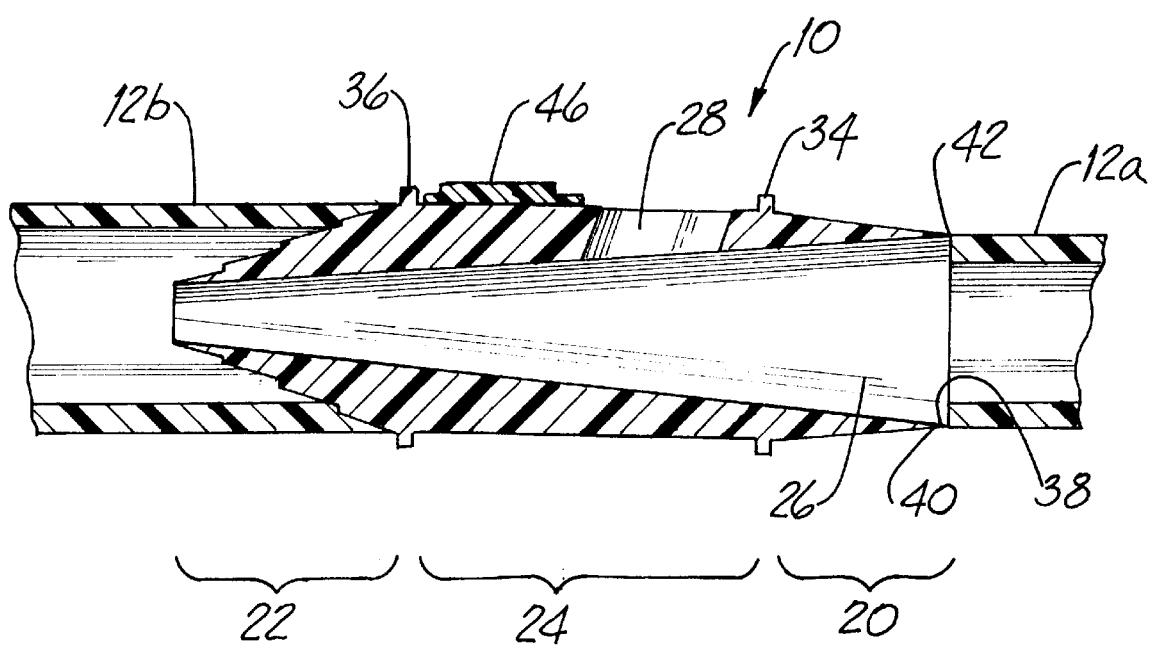
FIG. 7 is a sectional view of the suction pump connector valve and the pliable tube extending along the flowline showing the lateral flow path, tapered channel, and "sharp" edge of the upstream portion of the main body.

As shown in FIGS. 3 and 7, the upstream end portion 20 of the main body 18 is tapered and has an inner wall 38 and an outer wall 40 that converge so as to form a "sharp" edge 42 that fits snug against an inside wall of a pliable tube 12a extending along the flowline to the stomach 14. As used herein, the term "sharp" refers to a thin edge. Once fitted together, the upstream end portion 20 of the main body 18 is closely adjacent to the inside wall of the pliable tube 12a thereby reducing the possibility of particles becoming clogged along the flowline 12.

In a preferred embodiment of the invention, as shown in FIG. 3, the main flow path 26 is continuously tapered from the upstream end portion 20 of the main body 18 to the downstream end 22 of the main body 18 so that the main flow path 26 is substantially free of impediments whereby particles cannot collect along the main flow path 26. In this embodiment, the lateral flow path 28 is angled so as to allow for the easy insertion of a cleaning device.

Once positioned in the flowline 12, the device 10 is used to control suction to the patient. This is accomplished through the positioning of the controller 32 over the opening 30 by the operator. By varying the amount of the opening 30 that is occluded, the operator controls the amount of suction to the patient with full suction to the patient occurring when the opening 30 is fully occluded and no suction occurring to the patient when the opening 30 is fully unoccluded. In normal operation, the opening will be fully unoccluded when the operator desires to introduce fluids into the stomach.

While the principles of the invention have been shown and described in connection with but a few embodiments, it is to be understood clearly that such embodiments are by way of example and are not limiting.

For example, after analyzing this specification, persons of ordinary skill in the art will recognize that a bodily organ other than the stomach 14 can be used to define the upstream limit of the flowline 12.

I claim:

1. A stomach suction control device for placement in a flowline extending from a stomach upstream to a vacuum source downstream comprising:

a rigid main body having upstream and downstream end portions engageable with the flowline in fluid-flow relation thereto and having a middle exterior surface therebetween, the main body defining a main flow path extending therealong, such main flow path decreasing in cross-sectional area from the upstream to the downstream end, the main body also defining a lateral flow path extending from the main flow path to an opening in the middle exterior surface; and an imperforate controller attached to the main body and movable with respect to the opening to control whether, and the extent to which, the opening is blocked thereby.

2. The device of claim 1 wherein the controller is fitted around the middle exterior surface in a manner allowing the controller to move thereon over the opening.

3. The device of claim 2 wherein the controller is fitted around the middle exterior surface in a manner allowing the controller to move back and forth on the main body along the direction of the main flow path.

4. The device of claim 3 wherein the middle exterior surface is cylindrical and the controller partially encircles the middle exterior surface.

5. The device of claim 4 wherein the controller is retained on the middle exterior surface by a pair of spaced-apart tracks formed thereon and having the main flow path therebetween.

6. The device of claim 1 wherein the middle exterior surface of the main body is smooth and the controller has a smooth surface contacting the middle exterior surface, thereby permitting the controller to be moved in a continuum along the middle exterior surface.

7. The device of claim 6 wherein the controller is fitted around the middle exterior surface of the main body in a manner allowing the controller to move back and forth on the main body along the direction of the main flow path.

8. The device of claim 7 wherein the main body includes first and second stops affixed at the ends of the middle exterior surface to define the range of movement of the controller along the middle exterior surface.

9. The device of claim 1 wherein the upstream end portion of the main body has an inner wall and a smooth outer wall and said walls converge to form a sharp edge that fits snugly against and forms a smooth transition with an inside wall of a pliable tube extending along the flowline to the stomach.

10. The device of claim 9 wherein the upstream end portion of the main body is closely adjacent to the inside wall of the pliable tube.

11. The device of claim 1 wherein the main body has a single outer wall and a single inner wall and wherein the lateral flow path extends between the outer wall and the inner wall and is angled to allow easy insertion of a cleaning device.

12. A suction control device for placement in a flowline extending from a bodily organ upstream to a vacuum source downstream comprising:

a main body having upstream and downstream end portions engageable with the flowline in fluid-flow relation thereto and having a middle exterior surface therebetween, the main body defining a main flow path extending therealong, such main flow path decreasing in cross-sectional area from the upstream end portion to the downstream end portion, the main body also defining a lateral flow path extending from the main flow path to an opening in the middle exterior surface; and an imperforate controller attached to the main body and movable with respect to the opening to control whether, and the extent to which, the opening is blocked thereby.

* * * * *